United States Patent [19]
Popp et al.

[11] Patent Number: 5,895,382
[45] Date of Patent: Apr. 20, 1999

[54] FORESHORTENED CONTAINMENT FLAPS IN A DISPOSABLE ABSORBENT ARTICLE

[75] Inventors: Robert Lee Popp, Hortonville; Frank Steven Glaug, Appleton; Julia Mae Luben, Clintonville; Shirlee Ann Weber; David Arthur Kuen, both of Neenah, all of Wis.

[73] Assignee: Kimberly-Clark Worldwide, Inc., Neenah, Wis.

[21] Appl. No.: 08/054,508

[22] Filed: Apr. 26, 1993

[51] Int. Cl.$^6$ .................................................. A61F 13/15
[52] U.S. Cl. ........................................ 604/385.2; 604/385.1
[58] Field of Search .......................... 604/385.1, 385.2, 604/394–396, 398, 400–406

[56] References Cited

U.S. PATENT DOCUMENTS

| | | |
|---|---|---|
| Re. 26,151 | 1/1967 | Duncan et al. . |
| Re. 28,483 | 7/1975 | Ralph . |
| Re. 30,057 | 7/1979 | Schaar . |
| Re. 33,106 | 11/1989 | Beckestrom .................. 604/385.2 |
| 50,308 | 10/1865 | Ware . |
| 188,940 | 3/1877 | Packscher . |
| 1,001,940 | 8/1911 | Epstein . |
| 1,201,860 | 10/1916 | Nelke . |
| 1,419,044 | 6/1922 | Gunderson . |
| 1,508,740 | 9/1924 | Brand . |
| 1,655,300 | 1/1928 | Vizzard . |
| 1,971,671 | 8/1934 | Alsop . |
| 1,977,604 | 10/1934 | Alsop . |
| 2,004,088 | 6/1935 | Alsop . |
| 2,026,158 | 12/1935 | Bennett . |
| 2,052,598 | 9/1936 | Berg . |
| 2,078,512 | 4/1937 | Simpson . |
| 2,102,359 | 12/1937 | Frieman . |
| 2,141,105 | 12/1938 | Eller et al. . |
| 2,166,012 | 7/1939 | Maida . |
| 2,201,255 | 5/1940 | Wilson, Jr. . |
| 2,252,019 | 8/1941 | Meinecke et al. . |
| 2,252,992 | 8/1941 | Steiner . |
| 2,261,810 | 11/1941 | Reiner . |
| 2,266,518 | 12/1941 | Sarge . |
| 2,317,768 | 4/1943 | Holland et al. . |

(List continued on next page.)

FOREIGN PATENT DOCUMENTS

| | | |
|---|---|---|
| B86044/82 | 1/1983 | Australia . |
| B21332/83 | 5/1984 | Australia . |
| A45217/85 | 2/1986 | Australia . |
| 188667 | 4/1956 | Austria . |
| 1175602 | 10/1984 | Canada . |
| 1211902 | 9/1986 | Canada . |
| 1216702 | 1/1987 | Canada . |
| 1238151 | 6/1988 | Canada . |
| 1302654 | 6/1992 | Canada . |
| 0070584A1 | 1/1983 | European Pat. Off. . |
| 0098512A2 | 1/1984 | European Pat. Off. . |
| 0109126B1 | 5/1984 | European Pat. Off. . |
| 0149999A2 | 7/1985 | European Pat. Off. . |
| 0183668A2 | 6/1986 | European Pat. Off. . |
| 0190881A2 | 8/1986 | European Pat. Off. . |
| 0203712B1 | 12/1986 | European Pat. Off. . |
| 0219326B1 | 4/1987 | European Pat. Off. . |
| 0091412B2 | 5/1987 | European Pat. Off. . |
| 0243013B1 | 10/1987 | European Pat. Off. . |
| 0130848B1 | 11/1987 | European Pat. Off. . |
| 0251332A2 | 1/1988 | European Pat. Off. . |
| 0263720B1 | 4/1988 | European Pat. Off. . |
| 0264238A1 | 4/1988 | European Pat. Off. . |
| 0264952A2 | 4/1988 | European Pat. Off. . |
| 0268858A2 | 6/1988 | European Pat. Off. . |
| 0134086B1 | 1/1989 | European Pat. Off. . |

(List continued on next page.)

*Primary Examiner*—John G. Weiss
*Assistant Examiner*—K. M. Reichle
*Attorney, Agent, or Firm*—Douglas L. Miller

[57] ABSTRACT

A disposable absorbent article includes a waste containment assembly that has a liner, outer cover, and an absorbent between the liner and outer cover, and a pair of containment flaps that are operatively joined in a foreshortened state to the waste containment assembly. Methods are provided for making the absorbent article.

5 Claims, 9 Drawing Sheets

U.S. PATENT DOCUMENTS

| | | |
|---|---|---|
| 2,397,641 | 4/1946 | Blair . |
| 2,419,867 | 4/1947 | Woodman . |
| 2,435,945 | 2/1948 | Redmond . |
| 2,468,445 | 4/1949 | Hurst . |
| 2,494,261 | 1/1950 | Owenby . |
| 2,509,674 | 5/1950 | Cohen . |
| 2,538,596 | 1/1951 | Sheridan . |
| 2,538,758 | 1/1951 | Bricmont . |
| 2,544,069 | 3/1951 | Cutler . |
| 2,545,674 | 3/1951 | Ralph . |
| 2,575,164 | 11/1951 | Donovan . |
| 2,616,427 | 11/1952 | Pettit . |
| 2,662,526 | 12/1953 | Sanford . |
| 2,675,805 | 4/1954 | Trimble . |
| 2,787,271 | 4/1957 | Clark . |
| 2,827,052 | 3/1958 | Goodman et al. . |
| 2,840,077 | 6/1958 | Morgan . |
| 2,893,393 | 7/1959 | Pressley . |
| 2,895,477 | 7/1959 | Bernard . |
| 2,916,037 | 12/1959 | Hansen . |
| 2,921,583 | 1/1960 | Lerner . |
| 2,951,481 | 9/1960 | Gordon . |
| 2,964,040 | 12/1960 | Ashton et al. . |
| 2,969,065 | 1/1961 | Farnsworth . |
| 3,000,381 | 9/1961 | Mulhole et al. . |
| 3,087,495 | 4/1963 | Hart . |
| 3,098,484 | 7/1963 | Younger . |
| 3,142,301 | 7/1964 | Erteszek . |
| 3,180,335 | 4/1965 | Duncan et al. . |
| 3,182,661 | 5/1965 | Ribeiro et al. . |
| 3,237,625 | 3/1966 | Johnson . |
| 3,349,769 | 10/1967 | Piekarski . |
| 3,364,931 | 1/1968 | Hirsch . |
| 3,368,563 | 2/1968 | Scheier . |
| 3,386,442 | 6/1968 | Sabee . |
| 3,386,446 | 6/1968 | Sloan . |
| 3,397,696 | 8/1968 | Rickard . |
| 3,417,751 | 12/1968 | Murdoch . |
| 3,424,162 | 1/1969 | Parravicini . |
| 3,426,756 | 2/1969 | Romanek . |
| 3,452,753 | 7/1969 | Sanford . |
| 3,461,872 | 8/1969 | McConnell et al. . |
| 3,481,337 | 12/1969 | Ruffo . |
| 3,509,881 | 5/1970 | Sabee . |
| 3,530,859 | 9/1970 | Heimowitz . |
| 3,532,093 | 10/1970 | Lovret . |
| 3,572,342 | 3/1971 | Lindquist et al. . |
| 3,575,174 | 4/1971 | Mogor . |
| 3,592,194 | 7/1971 | Duncan . |
| 3,593,716 | 7/1971 | Vogt . |
| 3,599,640 | 8/1971 | Larson . |
| 3,612,055 | 10/1971 | Mesek et al. . |
| 3,613,687 | 10/1971 | Kennedy . |
| 3,658,063 | 4/1972 | Schaar . |
| 3,658,064 | 4/1972 | Pociluyko . |
| 3,665,920 | 5/1972 | Davis . |
| 3,667,466 | 6/1972 | Ralph . |
| 3,687,141 | 8/1972 | Matsuda . |
| 3,744,494 | 7/1973 | Marsan . |
| 3,765,418 | 10/1973 | Jones, Sr. . |
| 3,768,481 | 10/1973 | Shibata . |
| 3,771,524 | 11/1973 | Ralph . |
| 3,776,233 | 12/1973 | Schaar . |
| 3,779,246 | 12/1973 | Mesek et al. . |
| 3,807,402 | 4/1974 | Miller et al. . |
| 3,825,006 | 7/1974 | Ralph . |
| 3,848,594 | 11/1974 | Buell . |
| 3,860,003 | 1/1975 | Buell ................... 604/385.2 |
| 3,881,488 | 5/1975 | Delanty et al. . |
| 3,884,234 | 5/1975 | Taylor . |
| 3,885,568 | 5/1975 | Schaar . |
| 3,890,973 | 6/1975 | Davis et al. . |
| 3,901,236 | 8/1975 | Assarsson et al. ............... 128/284 |
| 3,913,578 | 10/1975 | Schaar . |
| 3,920,017 | 11/1975 | Karami . |
| 3,929,134 | 12/1975 | Karami . |
| 3,930,090 | 12/1975 | Campbell, Sr. et al. . |
| 3,930,501 | 1/1976 | Schaar . |
| 3,930,502 | 1/1976 | Tritsch . |
| 3,943,930 | 3/1976 | Schaar . |
| 3,952,745 | 4/1976 | Duncan . |
| 3,965,906 | 6/1976 | Karami . |
| 3,978,861 | 9/1976 | Schaar . |
| 3,987,794 | 10/1976 | Schaar . |
| 3,995,637 | 12/1976 | Schaar . |
| 3,995,640 | 12/1976 | Schaar . |
| 3,999,547 | 12/1976 | Hernandez . |
| 3,999,548 | 12/1976 | Hernandez . |
| 4,029,100 | 6/1977 | Karami . |
| 4,031,568 | 6/1977 | Huff . |
| 4,040,423 | 8/1977 | Jones, Sr. ...................... 128/287 |
| 4,041,950 | 8/1977 | Jones, Sr. . |
| 4,044,769 | 8/1977 | Papajohn . |
| 4,050,462 | 9/1977 | Woon et al. . |
| 4,067,068 | 1/1978 | Bregstein et al. . |
| 4,069,822 | 1/1978 | Buell . |
| 4,076,663 | 2/1978 | Masuda et al. .............. 260/17.4 GC |
| 4,081,301 | 3/1978 | Buell . |
| 4,090,515 | 5/1978 | Karami . |
| 4,100,324 | 7/1978 | Anderson et al. . |
| 4,100,922 | 7/1978 | Hernandez . |
| 4,122,552 | 10/1978 | Tedford . |
| 4,129,132 | 12/1978 | Butterworth et al. . |
| 4,166,464 | 9/1979 | Korpman . |
| 4,182,336 | 1/1980 | Black . |
| 4,187,342 | 2/1980 | Holst et al. . |
| 4,200,102 | 4/1980 | Duhamel et al. . |
| 4,205,679 | 6/1980 | Repke et al. ..................... 604/385.2 |
| 4,210,143 | 7/1980 | De Jonckheere . |
| 4,210,144 | 7/1980 | Sarge, III et al. . |
| 4,226,238 | 10/1980 | Bianco . |
| 4,227,531 | 10/1980 | McLeod . |
| 4,227,952 | 10/1980 | Sabee . |
| 4,232,674 | 11/1980 | Melican . |
| 4,239,578 | 12/1980 | Gore . |
| 4,246,900 | 1/1981 | Schroder . |
| 4,253,461 | 3/1981 | Strickland et al. . |
| 4,261,782 | 4/1981 | Teed . |
| 4,285,343 | 8/1981 | McNair . |
| 4,286,082 | 8/1981 | Tsubakimoto et al. ................ 526/240 |
| 4,309,236 | 1/1982 | Teed . |
| 4,315,508 | 2/1982 | Bolick . |
| 4,319,572 | 3/1982 | Widlund et al. . |
| 4,323,070 | 4/1982 | Ternstrom et al. . |
| 4,324,245 | 4/1982 | Mesek et al. . |
| 4,325,372 | 4/1982 | Teed . |
| 4,326,528 | 4/1982 | Ryan et al. . |
| 4,333,466 | 6/1982 | Matthews . |
| 4,351,340 | 9/1982 | McLeod . |
| 4,352,355 | 10/1982 | Mesek et al. ...................... 128/287 |
| 4,352,356 | 10/1982 | Tong . |
| 4,355,425 | 10/1982 | Jones et al. . |
| 4,388,075 | 6/1983 | Mesek et al. ..................... 604/385 |
| 4,397,645 | 8/1983 | Buell ............................ 604/380 |
| 4,407,284 | 10/1983 | Pieniak . |
| 4,413,996 | 11/1983 | Taylor ........................... 604/382 |
| 4,425,127 | 1/1984 | Suzuki et al. ................... 604/366 |
| 4,425,128 | 1/1984 | Motomura ...................... 604/381 |
| 4,425,173 | 1/1984 | Frick ............................ 156/204 |
| 4,427,408 | 1/1984 | Karami et al. ................... 604/393 |
| 4,430,086 | 2/1984 | Repke ............................ 604/385 |
| 4,486,192 | 12/1984 | Sigl . |

| Patent No. | Date | Inventor | Class |
|---|---|---|---|
| 4,488,927 | 12/1984 | Hooper | 156/464 |
| 4,490,148 | 12/1984 | Beckestrom | 604/385 |
| 4,496,359 | 1/1985 | Pigneul | 604/387 |
| 4,496,360 | 1/1985 | Joffe et al. | 604/397 |
| 4,498,944 | 2/1985 | Krause et al. | 156/205 |
| 4,500,316 | 2/1985 | Damico | 604/389 |
| 4,501,587 | 2/1985 | Enloe | 604/385 |
| 4,527,989 | 7/1985 | Karami . | |
| 4,555,245 | 11/1985 | Armbruster | 604/396 |
| 4,560,380 | 12/1985 | Tharel . | |
| 4,578,071 | 3/1986 | Buell | 604/379 |
| 4,578,073 | 3/1986 | Dysart et al. | 604/397 |
| 4,579,556 | 4/1986 | McFarland . | |
| 4,589,876 | 5/1986 | Van Tilburg . | |
| 4,597,760 | 7/1986 | Buell | 604/397 |
| 4,597,761 | 7/1986 | Buell | 604/397 |
| 4,601,717 | 7/1986 | Blevins | 604/358 A |
| 4,610,680 | 9/1986 | LaFleur . | |
| 4,610,681 | 9/1986 | Strohbeen et al. | 604/396 |
| 4,619,649 | 10/1986 | Roberts | 604/396 |
| 4,623,342 | 11/1986 | Ito et al. . | |
| 4,626,305 | 12/1986 | Suzuki et al. | 156/164 |
| 4,630,320 | 12/1986 | Van Gompel | 2/406 |
| 4,636,207 | 1/1987 | Buell | 604/370 |
| 4,639,949 | 2/1987 | Ales et al. | 2/400 |
| 4,641,381 | 2/1987 | Heran et al. | 2/400 |
| 4,642,819 | 2/1987 | Ales et al. | 2/400 |
| 4,646,362 | 3/1987 | Heran et al. | 2/400 |
| 4,655,760 | 4/1987 | Morman et al. . | |
| 4,657,539 | 4/1987 | Hasse . | |
| 4,661,102 | 4/1987 | Shikata et al. | 604/385.2 |
| 4,671,793 | 6/1987 | Hults et al. . | |
| 4,681,579 | 7/1987 | Toussant et al. | 604/385 R |
| 4,687,477 | 8/1987 | Suzuki et al. | 604/385 A |
| 4,687,478 | 8/1987 | Van Tilburg | 604/387 |
| 4,690,681 | 9/1987 | Haunschild et al. | 604/396 |
| 4,692,163 | 9/1987 | Widlund et al. . | |
| 4,695,278 | 9/1987 | Lawson . | |
| 4,695,279 | 9/1987 | Steer | 604/397 |
| 4,701,171 | 10/1987 | Boland et al. . | |
| 4,701,177 | 10/1987 | Ellis et al. . | |
| 4,704,115 | 11/1987 | Buell . | |
| 4,704,116 | 11/1987 | Enloe | 604/385.2 |
| 4,710,187 | 12/1987 | Boland et al. . | |
| 4,718,902 | 1/1988 | Bonito | 604/396 |
| 4,735,622 | 4/1988 | Acuff et al. | 604/361 |
| 4,738,676 | 4/1988 | Osborn, III . | |
| 4,738,677 | 4/1988 | Foreman . | |
| 4,743,239 | 5/1988 | Cole . | |
| 4,743,241 | 5/1988 | Igaue et al. . | |
| 4,743,246 | 5/1988 | Lawson | 604/385 A |
| 4,745,636 | 5/1988 | Lunt | 2/402 |
| 4,747,846 | 5/1988 | Boland et al. . | |
| 4,747,896 | 5/1988 | Boland et al. | 604/385.1 |
| 4,753,646 | 6/1988 | Enloe . | |
| 4,762,521 | 8/1988 | Roessler et al. | 604/38 SA |
| 4,775,375 | 10/1988 | Aledo | 604/378 |
| 4,795,452 | 1/1989 | Blaney et al. | 604/385.1 |
| 4,795,454 | 1/1989 | Dragoo | 604/385.2 |
| 4,798,603 | 1/1989 | Meyer et al. | 604/378 |
| 4,808,177 | 2/1989 | DesMarais et al. | 604/385.1 |
| 4,808,178 | 2/1989 | Aziz et al. | 604/385.2 |
| 4,816,025 | 3/1989 | Foreman | 604/385.2 |
| 4,816,026 | 3/1989 | Richardson | 604/385.2 |
| 4,822,435 | 4/1989 | Igaue et al. | 156/164 |
| 4,834,738 | 5/1989 | Kielpikowski et al. | 604/398 |
| 4,834,740 | 5/1989 | Suzuki et al. | 604/385.2 |
| 4,846,823 | 7/1989 | Enloe | 604/385.2 |
| 4,846,825 | 7/1989 | Enloe et al. | 604/385.1 |
| 4,850,990 | 7/1989 | Huntoon et al. | 604/385.2 |
| 4,861,652 | 8/1989 | Lippert et al. | 428/284 |
| 4,880,420 | 11/1989 | Pomparelli | 604/385.1 |
| 4,883,480 | 11/1989 | Huffman et al. | 604/385.1 |
| 4,883,482 | 11/1989 | Gandrez et al. | 604/385.2 |
| 4,892,528 | 1/1990 | Suzuki et al. | 604/385.2 |
| 4,895,568 | 1/1990 | Enloe | 604/385.2 |
| 4,900,317 | 2/1990 | Buell | 604/370 |
| 4,900,384 | 2/1990 | Sanders et al. | 604/385.2 |
| 4,904,251 | 2/1990 | Igaue et al. | 604/385.2 |
| 4,909,803 | 3/1990 | Aziz et al. | 604/385.2 |
| 4,909,804 | 3/1990 | Douglas, Sr. | 604/385.2 |
| 4,916,005 | 4/1990 | Lippert et al. | 428/192 |
| 4,917,696 | 4/1990 | De Jonckheere | 604/385.2 |
| 4,938,753 | 7/1990 | Van Gompel et al. | 604/385.2 |
| 4,938,754 | 7/1990 | Mesek | 604/385.2 |
| 4,938,755 | 7/1990 | Foreman | 604/385.2 |
| 4,938,757 | 7/1990 | Van Gompel et al. | 604/396 |
| 4,940,464 | 7/1990 | Van Gompel et al. | 604/385.2 |
| 4,988,344 | 1/1991 | Reising et al. | 604/368 |
| 5,021,051 | 6/1991 | Hiuke | 604/385.2 |
| 5,030,303 | 7/1991 | Cucuzza | 156/164 |
| 5,032,120 | 7/1991 | Freeland et al. | 604/385.2 |
| 5,080,658 | 1/1992 | Igaue et al. | 604/385.2 |
| 5,085,654 | 2/1992 | Buell | 604/370 |
| 5,087,255 | 2/1992 | Sims | 604/385.1 |
| 5,114,420 | 5/1992 | Igaue et al. . | |
| 5,167,653 | 12/1992 | Igaue et al. | 604/385.2 |
| 5,188,627 | 2/1993 | Igaue et al. | 604/385.2 |
| 5,190,606 | 3/1993 | Merkatoris et al. | 156/164 |
| 5,236,430 | 8/1993 | Bridges et al. | 604/396 |
| 5,246,431 | 9/1993 | Minetola et al. | 604/385.2 |
| 5,246,432 | 9/1993 | Suzuki et al. | 604/385.2 |
| 5,246,433 | 9/1993 | Hasse et al. | 604/396 |
| 5,304,159 | 4/1994 | Tanji et al. | 604/385.2 |
| 5,462,541 | 10/1995 | Bruemmer et al. | 604/391 |

FOREIGN PATENT DOCUMENTS

| | | | |
|---|---|---|---|
| 0304631A1 | 3/1989 | European Pat. Off. . | |
| 0309246A1 | 3/1989 | European Pat. Off. . | |
| 0311333A2 | 4/1989 | European Pat. Off. . | |
| 0323634A3 | 7/1989 | European Pat. Off. . | |
| 0324133A1 | 7/1989 | European Pat. Off. . | |
| 0329160A2 | 8/1989 | European Pat. Off. . | |
| 0346477A1 | 12/1989 | European Pat. Off. . | |
| 0374640A2 | 6/1990 | European Pat. Off. . | |
| 0376022A2 | 7/1990 | European Pat. Off. . | |
| 0386815A2 | 9/1990 | European Pat. Off. . | |
| 0391476A2 | 10/1990 | European Pat. Off. . | |
| 0409149A1 | 1/1991 | European Pat. Off. . | |
| 0456885A1 | 11/1991 | European Pat. Off. . | |
| 0 486 006 | 5/1992 | European Pat. Off. | A61F 13/15 |
| 0539703A1 | 5/1993 | European Pat. Off. . | |
| 0549988A1 | 7/1993 | European Pat. Off. . | |
| 358765 | 3/1906 | France . | |
| 1482677 | 5/1967 | France . | |
| 2425205 | 12/1979 | France . | |
| 2554325 | 5/1985 | France . | |
| 2557774 | 7/1985 | France . | |
| 2561078 | 9/1985 | France . | |
| 2573629 | 5/1986 | France . | |
| 1070779 | 12/1959 | Germany . | |
| 1435861 | 2/1969 | Germany . | |
| 2455778 | 6/1975 | Germany . | |
| 2521621 | 12/1975 | Germany . | |
| 2629560 | 1/1977 | Germany . | |
| 3039940A1 | 6/1981 | Germany . | |
| 3130716A1 | 3/1982 | Germany . | |
| 3216170A1 | 12/1982 | Germany . | |
| 2454590C2 | 1/1983 | Germany . | |
| 3319043A1 | 11/1984 | Germany . | |
| 3439775A1 | 5/1985 | Germany . | |
| 2521621C2 | 10/1985 | Germany . | |
| 2657220C2 | 3/1987 | Germany . | |
| 2657221C2 | 3/1987 | Germany . | |

| | | | | | | |
|---|---|---|---|---|---|---|
| 3141963C2 | 7/1988 | Germany. | | 3-207358 | 9/1991 | Japan. |
| 3128828C2 | 11/1989 | Germany. | | 3-218752 | 9/1991 | Japan. |
| 41-18359 | 8/1966 | Japan. | | 3-231660 | 10/1991 | Japan. |
| 41-18031 | 8/1976 | Japan. | | 3-234257 | 10/1991 | Japan. |
| 63-12702 | 1/1988 | Japan. | | 3/101935 | 10/1991 | Japan. |
| 63-12705 | 1/1988 | Japan. | | 3-268753 | 11/1991 | Japan. |
| 63-21901 | 1/1988 | Japan. | | 3-280951 | 12/1991 | Japan. |
| 63-105102 | 5/1988 | Japan. | | 3-286760 | 12/1991 | Japan. |
| 63-112702 | 5/1988 | Japan. | | 4-22359 | 1/1992 | Japan. |
| 63-112703 | 5/1988 | Japan. | | 4-5825 | 1/1992 | Japan. |
| 63-112705 | 5/1988 | Japan. | | 4-9153 | 1/1992 | Japan. |
| 63-112706 | 5/1988 | Japan. | | 4-67864 | 3/1992 | Japan. |
| 63-190002 | 8/1988 | Japan. | | 4-92665 | 3/1992 | Japan. |
| 63/230164 | 9/1988 | Japan. | | 4-122256 | 4/1992 | Japan. |
| 64-18105 | 1/1989 | Japan. | | 4-40625 | 4/1992 | Japan. |
| 64-18106 | 1/1989 | Japan. | | 4-42815 | 4/1992 | Japan. |
| 64-26701 | 1/1989 | Japan. | | 4-42816 | 4/1992 | Japan. |
| 64-26310 | 2/1989 | Japan. | | 4-47428 | 4/1992 | Japan. |
| 64-68503 | 3/1989 | Japan. | | 4-150853 | 5/1992 | Japan. |
| 64-77607 | 3/1989 | Japan. | | 4-152947 | 5/1992 | Japan. |
| 1-162806 | 6/1989 | Japan. | | 4200543 | 7/1992 | Japan. |
| 1-162807 | 6/1989 | Japan. | | 4-218157 | 8/1992 | Japan. |
| 1-162808 | 6/1989 | Japan. | | 4-218159 | 8/1992 | Japan. |
| 1-168903 | 7/1989 | Japan. | | 4-224750 | 8/1992 | Japan. |
| 1-183501 | 7/1989 | Japan. | | 4-90322 | 8/1992 | Japan. |
| 1-213402 | 8/1989 | Japan. | | 4-99921 | 8/1992 | Japan. |
| 1-246402 | 10/1989 | Japan. | | 4-120731 | 10/1992 | Japan. |
| 1-173106 | 12/1989 | Japan. | | 4-295356 | 10/1992 | Japan. |
| 2-65859 | 3/1990 | Japan. | | 4-325153 | 11/1992 | Japan. |
| 2-65861 | 3/1990 | Japan. | | 5-184622 | 7/1993 | Japan. |
| 2-107249 | 4/1990 | Japan. | | 358765 | 10/1931 | United Kingdom. |
| 2-58425 | 4/1990 | Japan. | | 667483 | 3/1952 | United Kingdom. |
| 2-58426 | 4/1990 | Japan. | | 790062 | 2/1958 | United Kingdom. |
| 2-58427 | 4/1990 | Japan. | | 849573 | 9/1960 | United Kingdom. |
| 2-126850 | 5/1990 | Japan. | | 1428572 | 3/1976 | United Kingdom. |
| 2-142564 | 5/1990 | Japan. | | 1453870 | 10/1976 | United Kingdom. |
| 2-142565 | 5/1990 | Japan. | | 1482677 | 8/1977 | United Kingdom. |
| 2-63834 | 5/1990 | Japan. | | 1520017 | 8/1978 | United Kingdom. |
| 2-71521 | 5/1990 | Japan. | | 1520018 | 8/1978 | United Kingdom. |
| 2-152450 | 6/1990 | Japan. | | 1520740 | 8/1978 | United Kingdom. |
| 2-152451 | 6/1990 | Japan. | | 1543915 | 4/1979 | United Kingdom. |
| 2-152452 | 6/1990 | Japan. | | 2023431 | 1/1980 | United Kingdom. |
| 2-156946 | 6/1990 | Japan. | | 2051557 | 1/1981 | United Kingdom. |
| 2-164362 | 6/1990 | Japan. | | 2063677 | 6/1981 | United Kingdom. |
| 2/164361 | 6/1990 | Japan. | | 2080093 | 2/1982 | United Kingdom. |
| 2-174845 | 7/1990 | Japan. | | 2101468 | 1/1983 | United Kingdom. |
| 2-191452 | 7/1990 | Japan. | | 2103093 | 2/1983 | United Kingdom. |
| 2-84623 | 7/1990 | Japan. | | 2149289 | 6/1985 | United Kingdom. |
| 2-271863 | 11/1990 | Japan. | | 2159693 | 12/1985 | United Kingdom. |
| 2-274250 | 11/1990 | Japan. | | 2161059 | 1/1986 | United Kingdom. |
| 3-21238 | 1/1991 | Japan. | | 2188532 | 10/1987 | United Kingdom. |
| 3-4850 | 1/1991 | Japan. | | 2193625 | 2/1988 | United Kingdom. |
| 3-59 | 1/1991 | Japan. | | 2196834 | 5/1988 | United Kingdom. |
| 3-224558 | 3/1991 | Japan. | | 2197181 | 5/1988 | United Kingdom. |
| 3-24118 | 3/1991 | Japan. | | 2215986 | 4/1989 | United Kingdom. |
| 3-60656 | 3/1991 | Japan. | | 2212382 | 7/1989 | United Kingdom. |
| 3-80858 | 4/1991 | Japan. | | 2216393 | 10/1989 | United Kingdom. |
| 3-90149 | 4/1991 | Japan. | | 2241871 | 9/1991 | United Kingdom. |
| 3-111048 | 5/1991 | Japan. | | 2242610 | 10/1991 | United Kingdom. |
| 3-121069 | 5/1991 | Japan. | | 2244422 | 12/1991 | United Kingdom. |
| 3-123553 | 5/1991 | Japan. | | 2250921 | 6/1992 | United Kingdom. |
| 3-131253 | 6/1991 | Japan. | | 2251172 | 7/1992 | United Kingdom. |
| 3-133452 | 6/1991 | Japan. | | 2255896 | 11/1992 | United Kingdom. |
| 3-136653 | 6/1991 | Japan. | | 2265834 | 10/1993 | United Kingdom. |
| 3-136655 | 6/1991 | Japan. | | 2268389 | 1/1994 | United Kingdom. |
| 3-143443 | 6/1991 | Japan. | | WO88/05269 | 7/1988 | WIPO. |
| 3-151970 | 6/1991 | Japan. | | WO 90/14063 | 11/1990 | WIPO. |
| 3-60919 | 6/1991 | Japan. | | WO92/07533 | 5/1992 | WIPO. |
| 3-165761 | 7/1991 | Japan. | | 93/03698 | 3/1993 | WIPO. |
| 3-186261 | 8/1991 | Japan. | | WO9309739 | 5/1993 | WIPO. |
| 3-186262 | 8/1991 | Japan. | | WO9309742 | 5/1993 | WIPO. |
| 3-188851 | 8/1991 | Japan. | | WO9309746 | 5/1993 | WIPO. |
| 3-198851 | 8/1991 | Japan. | | WO93/17648 | 9/1993 | WIPO. |
| 3-202054 | 9/1991 | Japan. | | | | |

FORESHORTENED CONTAINMENT FLAPS IN A DISPOSABLE ABSORBENT ARTICLE

BACKGROUND OF THE INVENTION

This invention pertains to disposable absorbent articles, and more particularly to a child's training pant having improved containment flaps for providing improved containment and absorbency of waste matter.

Currently, disposable absorbent articles find widespread use in the areas of adult care, infant care, and child care, and have generally replaced reusable cloth articles. Disposable diapers have met a particular need and have become increasingly popular. However, even though these diapers are popular, they continue to have several problems. One of these problems pertains to the containment and absorbent features of the diaper. Although current disposable diapers have elasticized leg openings, these elasticized leg openings are not entirely successful in stopping leakage of urine or rapidly discharged liquid bowel movements.

One attempt to eliminate this leakage is the provision of a pair of containment flaps spaced inwardly of the elasticized leg openings. These flaps are intended to reduce the leakage of waste material at the elasticized leg openings. In practice, however, leakage still occurs.

Once a child reaches an age of about 15 to 30 months, a parent or caretaker generally desires to start toilet training so the child can become independent of the parent or caretaker. A training pant is intended for use when the child has reached an age at which he or she is ready to graduate to underpants, which are three-dimensional articles, as a replacement for disposable diapers, which are two-dimensional articles. A suitable disposable training pant is an article having closed sides so that a child will raise and lower the pant as necessary without requiring, hopefully, the aid of a parent. A child puts the training pant on by placing his or her feet in the respective leg openings and pulling the pant upwardly along the legs to fit the pant snugly at the crotch. This is significantly different from the way a diaper is fitted.

Although it is hoped by the parent that the child will not have an accident while wearing a training pant, it is highly probable that it will occur. Thus, there is a need to provide an improved child's training pant that will absorb and contain body waste, and do so in a manner that reduces, if not eliminates, leakage.

SUMMARY OF THE INVENTION

In one embodiment of the present invention there is provided a disposable absorbent article comprising a waste containment assembly and a pair of containment flaps operatively joined in a foreshortened state to said waste containment assembly.

In another embodiment of the present invention there is provided a disposable article comprising a waste containment assembly, elastic side panels operatively joined to said waste containment assembly to form a waist opening and a pair of leg openings, and a pair of containment flaps operatively joined in a foreshortened state to said waste containment assembly.

In still another embodiment of the present invention there is provided a disposable absorbent article comprising a waste containment assembly comprising an inner surface, a pair of sides, and forming a waist opening and a pair of leg openings; an elastic side member operatively joined to each said inner surface of each said side; and a pair of containment flaps operatively joined to said waste containment assembly.

In still yet another embodiment of the present invention there is provided a method of making a disposable absorbent article comprising the steps of providing a waste containment assembly, supplying a pair of containment flaps, foreshortening the containment flaps, and joining the containment flaps to the waste containment assembly.

In still further another embodiment of the present invention there is provided a method of making a disposable absorbent article comprising the steps of providing a waste containment assembly, supplying a pair of containment flaps, joining the pair of containment flaps to the waste containment assembly, and attaching elastic side panels to the waste containment assembly to form a waist opening and a pair of leg openings.

Another embodiment of the present invention provides a method of making a disposable absorbent article comprising the steps of providing a waste containment assembly comprising an inner surface and a pair of sides, attaching an elastic side member to the inner surface of each side, supplying a pair of containment flaps, joining the containment flaps to the waste containment assembly, and forming a waist opening and a pair of leg openings with portions of the sides of the waste containment assembly.

Still another embodiment of the present invention provides a disposable absorbent article comprising a waste containment assembly, elastic side panels operatively joined to said waste containment assembly to form a waist opening and a pair of leg openings, and a pair of containment flaps operatively joined to said waste containment assembly.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

DEFINITIONS

Within the context of this specification, each term or phrase below will include the following meaning or meanings:

(a) "SBL" means a stretch bonded laminate that is at least a two-layered composite in which one layer is a gatherable layer and the other layer is a stretchable, i.e., elastic, layer. The layers are joined together when the stretchable layer is in a stretched condition so that upon relaxing the layers, the gatherable layer is gathered.

(b) "Two-dimensional" refers to a garment that can be opened without destructively tearing any structure while being laid in a flat condition. These garments, such as diapers, do not have continuous leg and waist openings, and require a fastening device, such as adhesive tapes, to attach the garment about the wearer.

(c) "Three-dimensional" refers to a garment similar to shorts or pants in that they have continuous leg and waist openings that are bounded by material of which the garment is made. They may or may not have manually tearable seams.

(d) "Member" when used in the singular can have the dual meaning of a single element or a plurality of elements.

(e) "Operatively joined" with reference to the attachment of an elastic member to another element means that the elastic member when attached to or connected to or treated with heat with the element gives that element elastic properties. With reference to the attachment of a non-elastic member to another element, it means that the member and element can be attached in any suitable manner that permits or allows them to perform the intended or described function of the joinder. The joining, attaching, connecting or the like can be either directly, such as joining either member directly to an element, or can be indirectly by means of another member or element disposed between the first member and the first element.

(f) "Disposed", "disposed on", "disposed with", "disposed at", "disposed near", and variations thereof are intended to mean that one element can be integral with another element, or that one element can be separate structure joined to or connected to or placed with or placed near another element.

(g) "Disposable" includes being disposed of after use, and not intended to be washed and reused.

(h) "Foreshortened" and "foreshortening" include to shorten beforehand, i.e., before a subsequent step.

(i) "Force" includes a physical influence exerted by one body on another which produces acceleration of bodies that are free to move and deformation of bodies that are not free to move. Force is expressed in grams.

(j) "Tension" includes a uniaxial force tending to cause the extension of a body or the balancing force within that body resisting the extension.

(k) "Extension", "extend", and "extended" include the change in length of a material due to stretching. Extension is expressed in units of length.

(l) "Elongation" includes the ratio of the extension of a material to the length of a material prior to stretching. Elongation is expressed in percent.

(m) "Rupture" includes the breaking or tearing apart of a material; in tensile testing, rupture refers to the total separation of a material into two parts either all at once or in stages, or the development of a hole in some materials.

(n) "Ultimate elongation" includes the elongation at the point of rupture.

(o) "Elasticity" and "elastic" include that property of a material by virtue of which it tends to recover its original size and shape after removal of the force causing the deformation.

These definitions are not intended to be limiting, and these terms may be defined with additional language in the remaining portion of the specification.

DESCRIPTION OF A PREFERRED EMBODIMENT

Figure 1:
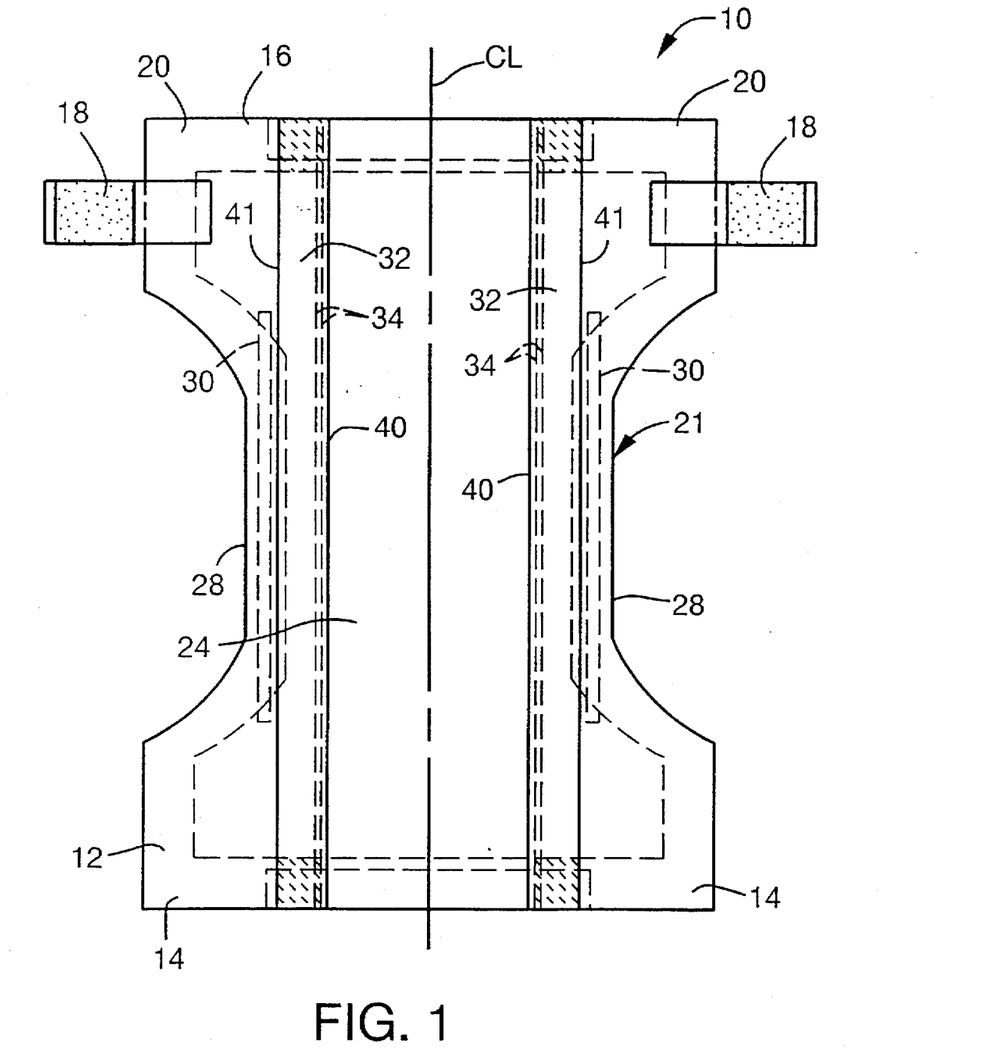
FIG. 1 is a top plan view of a diaper having conventional containment flaps.
Figure 2:
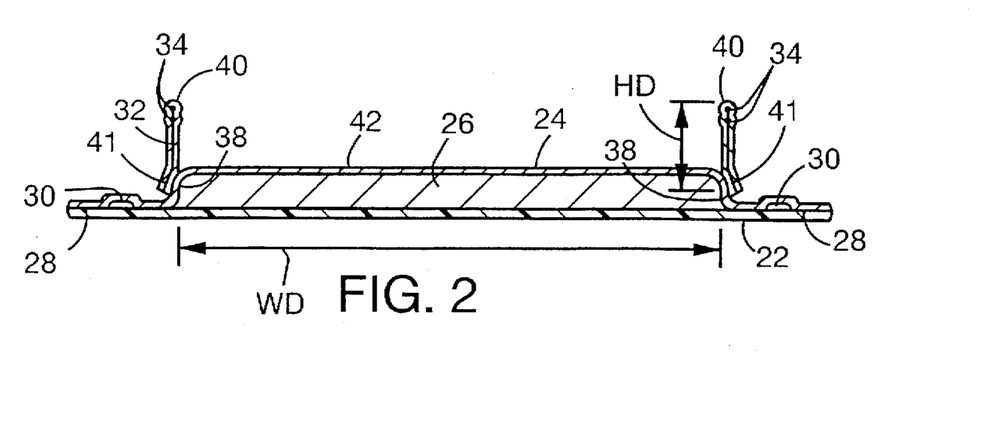
FIG. 2 is a cross-sectional view through the crotch area of the diaper in FIG. 1.
Figure 3:
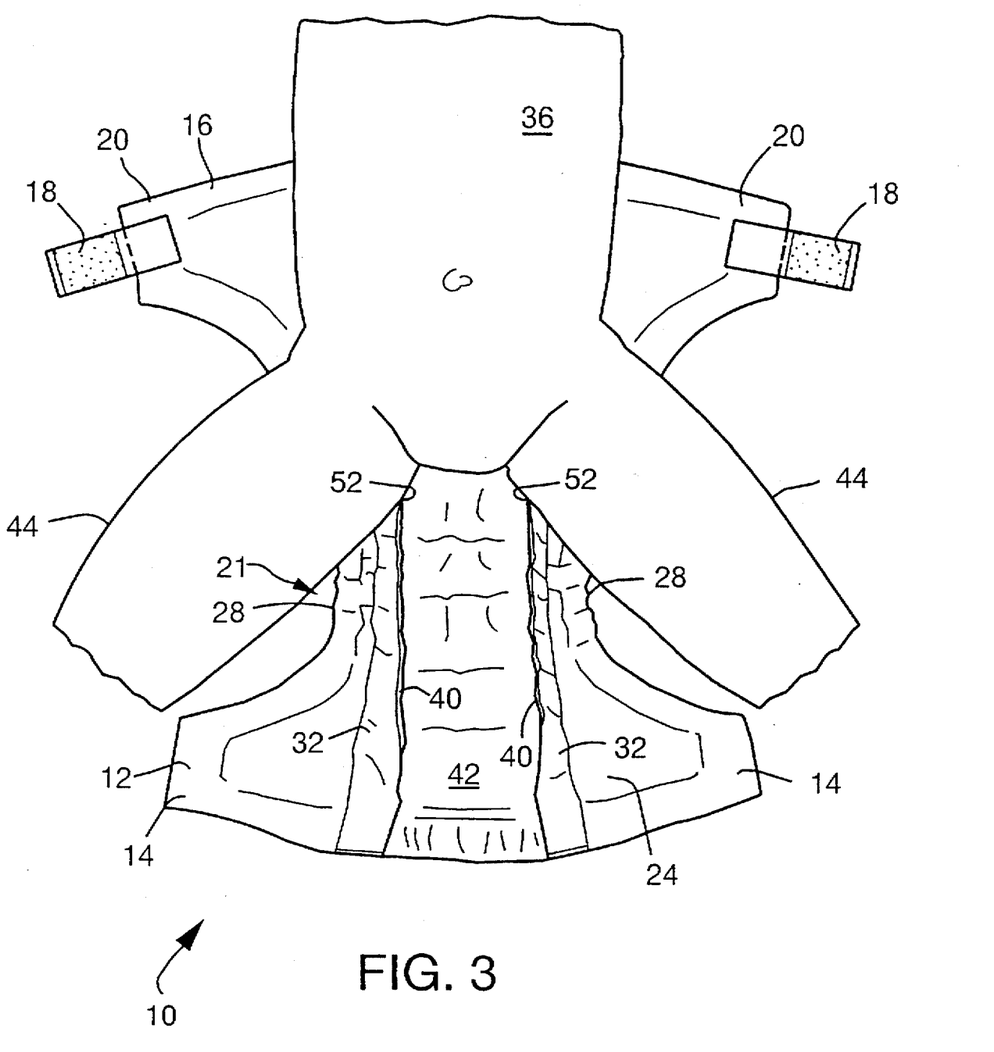
FIG. 3 is a perspective view illustrating a step in fitting the diaper of FIG. 1 on an infant.

Referring primarily to FIGS. 1–3, diaper 10 comprises front waist section 12 including oppositely disposed front ear sections 14, back waist section 16 including adhesive tapes 18 on respective oppositely disposed back ear sections 20, and crotch section 21 between front section 12 and back section 16. Diaper 10 further comprises a liquid impermeable back sheet 22, a liquid permeable bodyside liner 24, and an absorbent pad 26 disposed between back sheet 22 and liner 24. Extensions of back sheet 22 and liner 24 beyond the longitudinal edges or absorbent sides 38 of absorbent pad 26 form oppositely disposed side sections 28, which individually include an elastic member 30 adhesively attached between back sheet 22 and liner 24. Disposed inwardly of each side section 28 is a containment flap 32 having elastic members 34 adhesively attached thereto. Each containment flap 32 can be one layer of desired material that encloses elastic members 34 in any suitable manner known in the art. Elastic members 30 and elastic members 34 are attached in diaper 10 while in an extended condition in order to provide an elastic effect at side sections 28 and at the distal ends 40 of containment flaps 32. A more detailed description of the structure of a typical diaper 10, its process of manufacture, and method of use are contained in U.S. Pat. No. 4,704,116, which is assigned to the assignee of the present invention, the contents of which are incorporated by reference herein.

Referring specifically to FIG. 2, crotch width WD is measured between opposite absorbent sides 38 and along a line transverse, i.e., perpendicular, to the longitudinal direction of centerline CL. Each flap 32 has a height HD measured between distal end 40 and proximal end 41 at which flap 32 is joined or adhered to top surface 42 of liner 24. A proximal end is identified as that point of attachment or joining that is closest to its respective distal end. For example, if a containment flap is attached or adhered by three parallel lines of adhesive beads, then the proximal end is coincident with or starts at the adhesive bead closest to the distal end. Similarly, if the containment flap is adhered by a ribbon of adhesive, then the proximal end is coincident with or starts at the edge of the adhesive ribbon closest to the distal end. Height HD is far less in dimension than the width WD in diaper 10. The significance of this relationship will be described hereafter. In those diapers having containment flaps that are not attached to or near the sides 38 of the absorbent, the width dimension WD is that width between the points of attachment of proximal ends 41 of containment flaps 32 on the diaper. For example, if in FIG. 2, each flap 32 were to be attached to liner 24 just above an elastic member 30, then the measured width WD would be that distance between elastic members 30. In any event, it is important to note that height HD is far less than width WD. In some diapers the attachment or adhesive line joining the proximal end of a containment flap to a diaper may be curved in relation to the longitudinal centerline of that diaper. In these cases, widths WD between the points of attachment of the containment flaps will vary. However, a curved, attached containment flap can still result in the flap height HD being far less than the average distance between the points of attachment of the flaps to the diaper.

Referring now to FIG. 3, there is illustrated torso 36 of an infant that has been placed upon back waist section 16 of diaper 10 in preparation of fitting and attaching diaper 10 to torso 36. As illustrated, legs 44 of the infant are spread far apart so that front section 12 can be simply folded upwardly over the front of torso 36 and in a manner that snugly fits crotch section 21 against the infant. Thereafter, adhesive tapes 18 are attached to the outermost surface of respective front ear sections 14. Because of the wide crotch dimension of diaper 10 in relation to the infant's crotch width and the wide distance between containment flaps 32, flaps 32 contact initially the inner leg surfaces 52 of the thigh when diaper 10 is folded upwardly to fit between the legs. Containment flaps 32, upon contacting the inner leg surfaces of the thighs, can bend or turn outwardly away from the center of the diaper, which is not the desired position or shape of flaps 32. In order for containment flaps 32 to perform optimally, it is important they do not turn or bend outwardly since fluids, such as urine, can then wick along flaps 32, out of diaper 10, and along the legs of the wearer.

Figure 4:
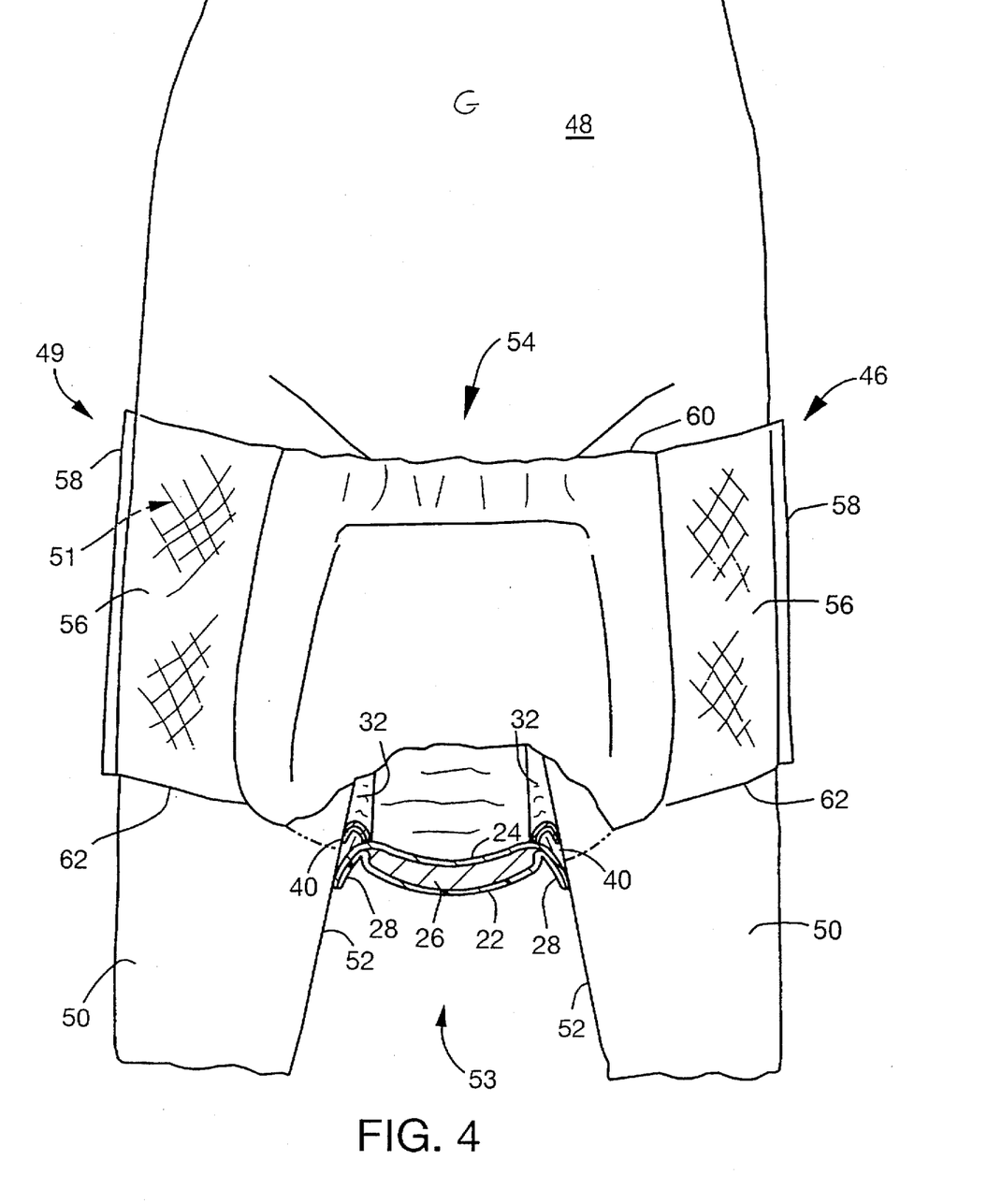
FIG. 4 is an elevational, partially broken-away view of a training pant at an intermediate point of its being pulled on and having the same type of containment flaps as the diaper of FIG. 1.

Turning now to FIG. 4, training pant 46 is illustrated as partially fitted, i.e., not pulled fully upwardly to the waist, on a child's torso 48. Torso 48 includes legs 50 that have respective inner surfaces 52 that extend from the ankle (not illustrated) to the perineum or crotch of torso 48. Training pant 46 can be made or constructed in a variety of ways, one of which is described in U.S. Pat. No. 4,940,464, which is incorporated by reference herein. Other training pant designs are described in U.S. Pat. Nos. 4,938,757 and 4,747,846, and in U.S. patent application Ser. No. 809,993 filed on Dec. 18, 1991; the contents of these two patents and one patent application being incorporated by reference herein.

Training pant 46 generally comprises waste containment section 54 joined in any suitable manner to side panels 56, which may or may not have elastic characteristics. Side panels 56, which are stretchable, i.e., elastic, in this embodiment (FIG. 4), are ultrasonically bonded to form manually tearable, non-refastenable seams 58. Training pant 46 further includes front end portion 49, back end portion 51, and crotch area 53 between end portions 49 and 51.

As illustrated in FIG. 4, waste containment section 54 includes the containment flaps 32 earlier described with reference to diaper 10, back sheet 22, liner 24, absorbent pad 26 between back sheet 22 and liner 24, and side sections 28. Containment flaps 32 have respective distal ends 40.

Several differences, both structural and functional, exist between a typical diaper, such as diaper 10, and a training pant, such as training pant 46. One of the differences is in the method of fitting the diaper to a baby and a training pant to a child. As described above, diaper 10, which is a two-dimensional article, is fitted on an infant by placing the infant on back waist section 16 (FIG. 3) and then folding front waist section 12 upwardly to be joined with back waist section 16 by adhesive tapes 18. In contrast, a three-dimensional article, such as training pant 46, is not fitted in the same manner. Training pant 46 is fitted by inserting the wearer's feet through waist opening 60 and respective leg openings 62 (FIG. 4), then grasping training pant 46 near waist opening 60, and pulling upwardly along the legs until crotch area 53 of training pant 46 is snugly fit against the crotch of the wearer. During the travel of training pant 46 upwardly along legs 50 and their inner surfaces 52, distal ends 40 of flaps 32 begin to turn or bend outwardly away from each other and then bend downwardly due to the sliding contact or friction between legs 50 and flaps 32. This position of flaps 32 is undesirable since urine can wick or transfer along and over containment flaps 32 and beyond side sections 28, thereby soiling both legs 50 and the clothes of the wearer.

It has been discovered that a mechanism causing this outward turning or bending of containment flaps 32 as they move upwardly along inner leg surfaces 52 is the relatively short height dimension HD of containment flaps 32 in relation to width dimension WD, the elasticity and tension provided by the flap elastics, and the length of attachment of the flap ends to the bodyside liner.

Figure 6:
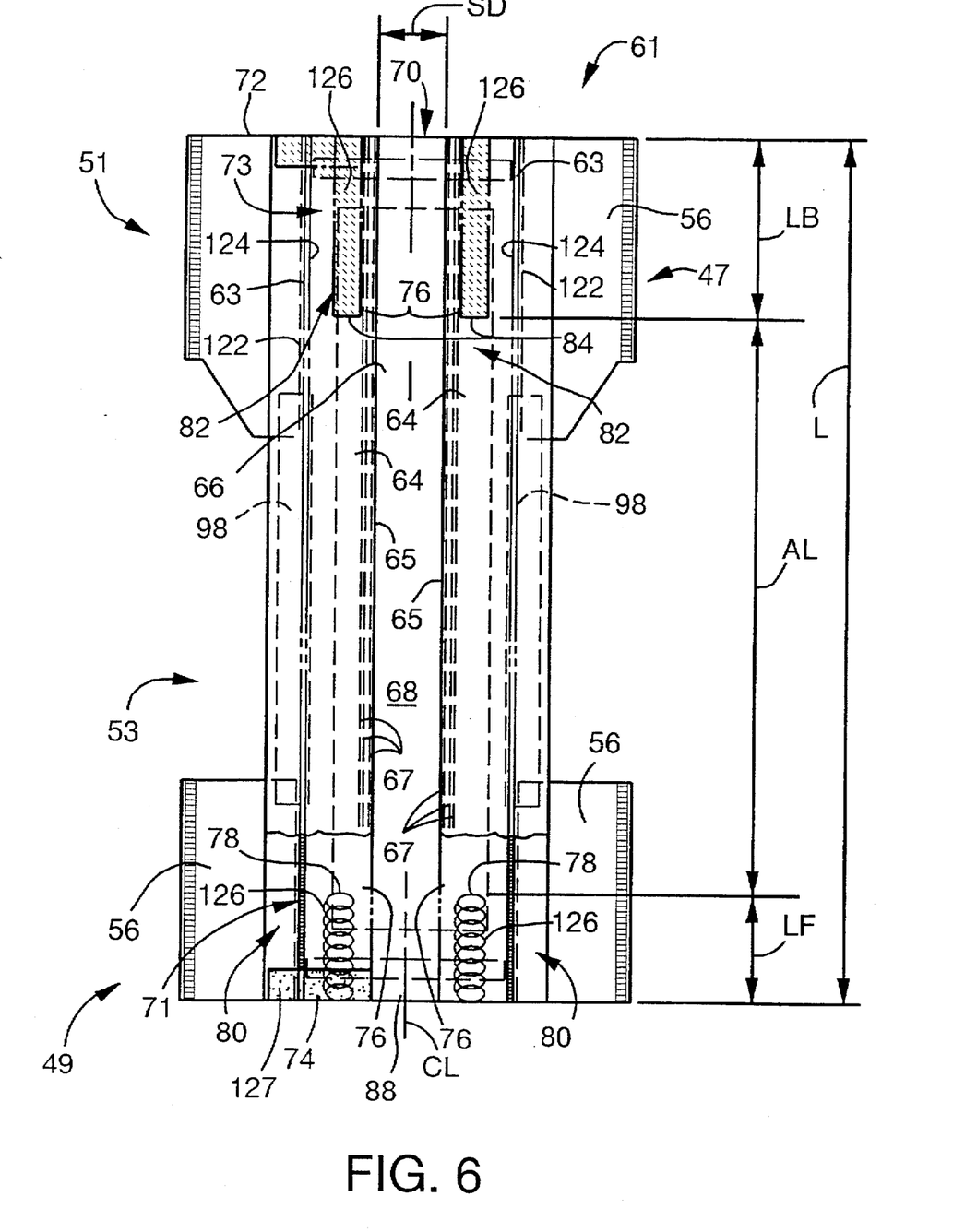
FIG. 6 is a partially disassembled, partially broken-away, stretched-flat top plan view of the embodiment in FIG. 5 illustrating two ways of attaching the containment flaps.
Figure 7:
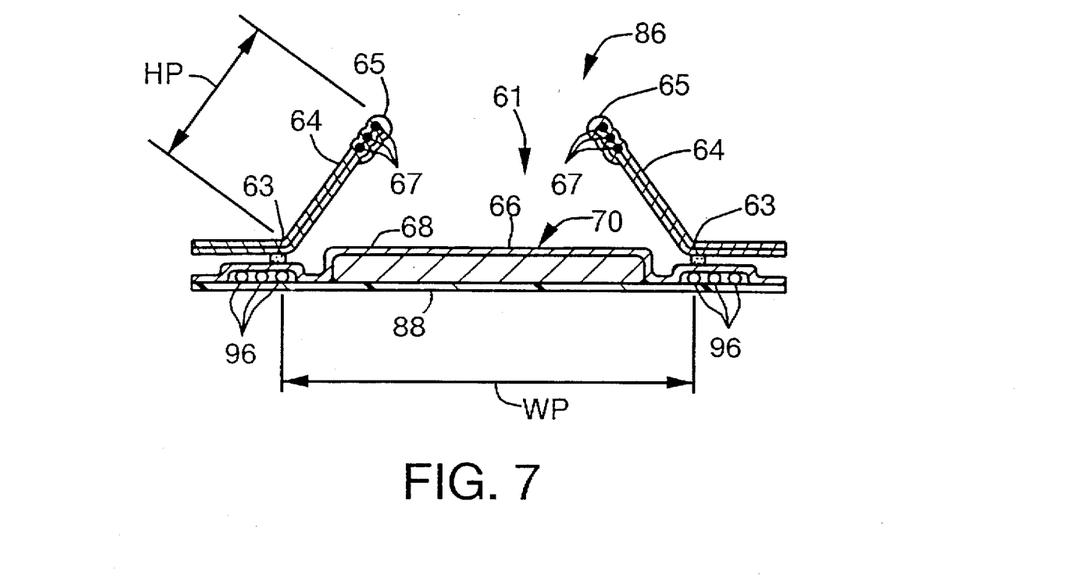
FIG. 7 is a cross-sectional view through the crotch area of the embodiment of FIG. 6 with the crotch area in a flat state, but with the containment flaps in an upright orientation.

Referring now to FIGS. 6 and 7, training pant 47 is illustrated with containment flaps 64 of the present invention incorporated with waste containment assembly 61 which includes liner 66, absorbent composite 70, and outer cover 88; waste containment assembly 61 also can include only absorbent composite 70 and outer cover 88, or can include additional structure such as a surge or other type of layer. Training pant 47 has containment flaps 64 attached to waste containment assembly 61, and although flaps 64 can be attached to outer cover 88 or any other structure of training pant 47, they are desirably attached to bodyside liner 66, such as its top surface 68. Each containment flap 64 has proximal end 63 adhesively attached to top surface 68, and flap elastics 67 adhesively attached in an extended condition at distal end 65. Pant 47 includes front end portion 49 and back end portion 51, and pant back edge 72 (FIG. 6) and pant front edge 74; the distance between edges 72, 74 define length L of training pant 47, and also can be the length of waste containment assembly 61.

Figure 5:
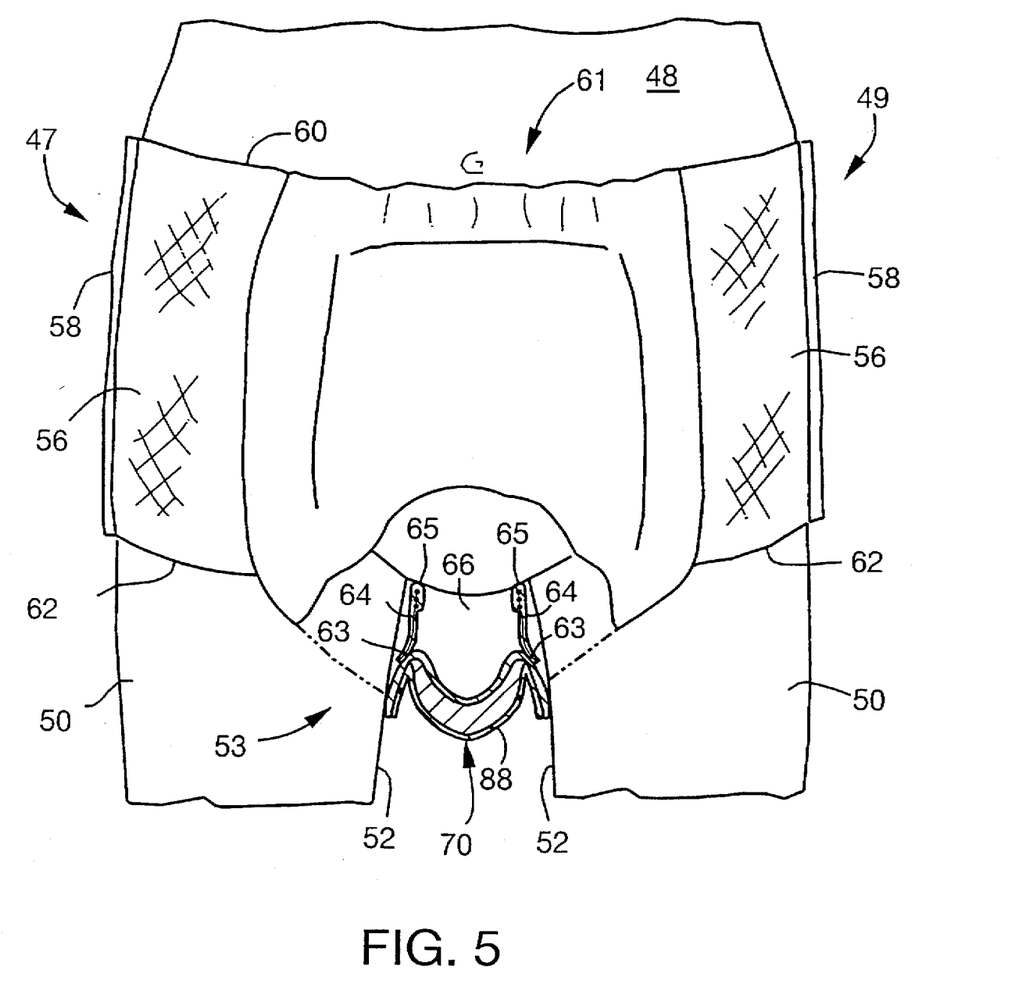
FIG. 5 is an elevational, partially broken-away view illustrating the present invention fitted on a child.

FIG. 6 illustrates training pant 47 in a flat state prior to its being folded to form seams 58 (FIG. 5) with side panels 56, which result in the finished training pant 47 having waist opening 60 (FIG. 5) and leg openings 62. The term "finished training pant" means a three-dimensional training pant that can be used for its intended purpose. FIG. 7 illustrates the upright position containment flaps 64 assume when pant 47 is being worn, and it is understood that, although waste containment assembly 61 is illustrated as being flat for the purpose of making it easier to see and understand the description of training pant 47, waste containment assembly 61 in fact assumes a bowed- or curved-like shape in the crotch as illustrated in FIG. 5.

Referring to FIGS. 6, 6A, 6B, and 7, each containment flap 64 extends the longitudinal length of training pant 47 between back edge 72 and front edge 74, and is attached to liner 66. Each containment flap 64 has a front end portion 71 and a back end portion 73 adhered to liner 66 such that distal ends 65 are adhered to liner 66 to prevent them from moving into the upright position.

Figure 6A:
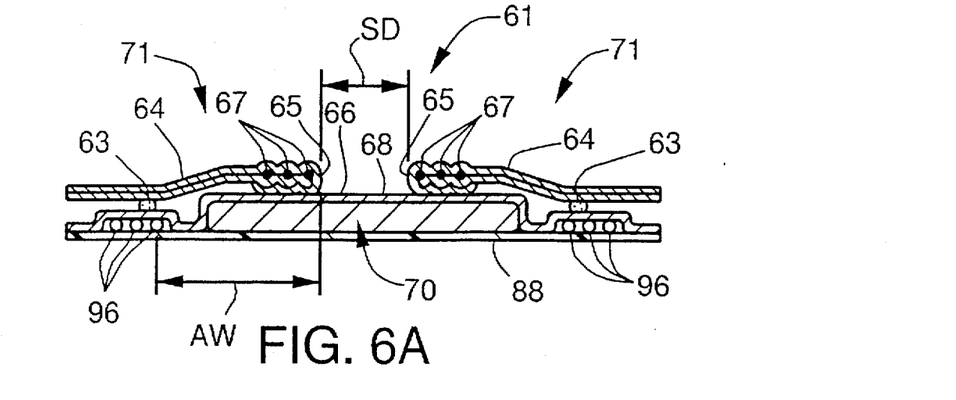
FIG. 6A is an enlarged cross-sectional view through a front end portion of the embodiment in FIG. 6 showing the containment flaps in a fully extended, adhered state in the transverse direction.

FIG. 6A illustrates front end portion 71 of each flap 64 in a fully extended, adhered state, in the transverse direction. Current absorbent articles with some type of containment flap have their flap adhered to the liner while in this or a similarly extended state in the transverse direction. The transverse distance as measured between distal ends 65 at either the front or back end portions 71, 73 is the flap separation distance SD. The term "transverse" means a direction or line perpendicular to center line CL (FIG. 6) of training pant 47.

Figure 6B:
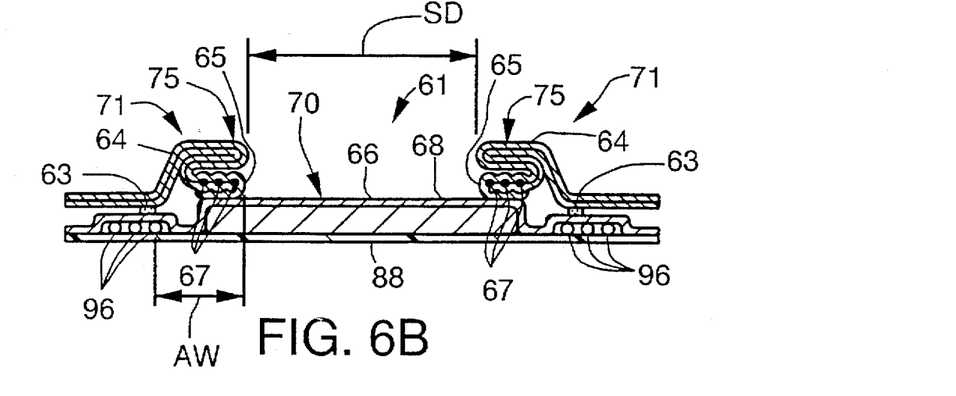
FIG. 6B is similar to FIG. 6A but showing the containment flaps in a foreshortened, adhered state at a front end portion in accordance with the principles of the present invention.

Unique to the present invention is the attachment of flap front end portion 71 and flap back end portion 73 to liner 66 as illustrated in FIG. 6B. At end portions 71, 73, distal ends 65 have been positioned or moved farther apart from each other before being adhered to liner 66, which increases the dimension or measurement of flap separation distance SD relative to its dimension or measurement as illustrated in FIG. 6A. To state the same in a different manner, each distal end 65 is moved closer to its respective proximal end 63 before being adhered to liner 66, thereby increasing flap separation distance SD. This moving, in the transverse direction, of distal ends 65 closer to their respective proximal end 63 is termed "foreshortening" flaps 64 before they are adhered to liner 66 at their respective front and back end portions 71, 73. Once flaps 64 have been foreshortened and attached to liner 66, portions of flaps 64 gather, and in FIG. 6B the gathering is illustrated as a Z-fold 75; fold 75 can take other shapes such as a U-shape or a series of micropleats. Even though each flap 64 is foreshortened at its end portions 71, 73, flap height HP (FIG. 7) is still measured in crotch area 53 between distal ends 65 and proximal ends 63 when flap 64 is in a flat state, as illustrated in FIGS. 6 and 7.

With reference to FIG. 6B, the transverse distance between an attached distal end 65 and an attached proximal end 63 at an end portion 71, 73 is the flap attached width AW. It now can be appreciated that with the same given flap attached width AW, the present invention provides a foreshortened containment flap 64 with a greater flap height HP than is available with articles having containment flaps attached in the conventional fully extended manner, as illustrated in FIG. 6A. Therefore, each containment flap 64 is able to assume a higher or taller upright orientation (FIGS. 5 and 7) which assists in containing urine and liquid bowel movements until absorbent composite 70 can fully absorb those wastes. This is important since absorbent composite 70 has a width that is between about three inches to about four inches in crotch area 53.

Furthermore, as absorbent composite 70 becomes heavier due to the added weight of absorbed wastes, it will tend to sag downwardly at the crotch. However, since flaps 64 have been foreshortened, they can extend, under the influence of flap elastics 67, to continue to seal at the crotch (FIG. 5).

It also now can be recognized that if containment flaps 64 have flap heights HP and are attached to liner 66 as illustrated in FIG. 6A, that distal ends 65 are closer together in comparison to their foreshortened attachment in FIG. 6B, and that this close proximity, i.e., a narrow flap separation distance SD (FIG. 6A), between distal ends 65 can continue to exist at the crotch of the wearer, which will result in some waste not passing between distal ends 65 to absorbent composite 70, but passing instead over the outermost sides of flaps 64 and thus along the legs and clothes of the wearer. By foreshortening flaps 64 in accordance with the present invention, flap separation distance SD can be controlled, i.e., made greater, to allow waste to pass between distal ends 65 into well 86 to absorbent composite 70.

Turning now to FIG. 6, the lower left broken-away corner of pant 47 shows one method of joining or attaching flap 64. Flap front attached length LF extends between front edge 74 and adhesive end edge 78 of flap end adhesive 126 (FIGS. 6 and 9), thereby forming a flap front dead zone 80. Within this front dead zone 80, containment flap 64 is adhered to liner 66 between front edge 74 and adhesive end edge 78 in the longitudinal direction by flap end adhesive 126, and between proximal end 63 and distal end 65 in the transverse direction by adhesive 127, so that distal end 65 does not assume an upright orientation. Similarly, the upper left corner of pant 47 (FIG. 6) has flap back dead zone 82 extending between back edge 72 and adhesive end edge 84, thereby defining flap back attached length LB. Flaps 64 are adhered at their ends to, among other things, control the spacing between distal ends 65, which define flap separation distance SD. Between flap front attached length LF and flap back attached length LB is active flap length AL in which flap elastics 67 cause distal end 65 of a flap 64 to assume an upright orientation, as illustrated in FIG. 7. Dead zones 80, 82 define four corners 76 (FIG. 6) where flaps 64 begin to assume an upright orientation, thereby forming well 86 (FIG. 7) for containing waste material, such as urine, which allows sufficient time for absorbent composite 70 to absorb the urine.

Still referring to FIG. 6, the lower right broken-away corner of training pant 47 shows another method of attaching a containment flap 64 in which adhesive 127 is absent. Although adhesive 127 is not present, flap end adhesive 126 still provides dead zones 80, 82 respectively along flap front attached length LF and flap back attached length LB.

As illustrated in FIG. 7, each containment flap 64 has a flap height HP measured between distal end 65 and proximal end 63 along the surface of flap 64, and a flap width WP measured between proximal ends 63 along a transverse line perpendicular to the longitudinal centerline CL of training pant 47.

Referring to FIGS. 6–7, flap front attached length LF has a range desirably between about 0.50 inches (about 12 mm) to about 11 inches (about 280 mm), and flap back attached length LB has a range desirably between about 0.50 inches (about 12 mm) to about 13 inches (about 330 mm). A distance for active flap length AL is desirably about 7 inches (about 178 mm) to about 41 inches (about 1,042 mm). A flap separation distance SD is desirably between about 1 inch (25.4 mm) to about 3 inches (76.2 mm). These dimensions are measured when training pant 47 is in a flat, stretched condition as illustrated in FIG. 6.

With reference to FIG. 7, flap height HP has a range between about 1 inch (25.4 mm) to about 3.0 inches (76.2 mm), and a desired range of about 1.25 inches (31.75 mm) to about 2.0 inches (50.8 mm).

Overall product length L is measured, as illustrated in FIG. 6, between back edge 72 and front edge 74, and length L is desirably between about 17 inches (about 432 mm) to about 42 inches (about 1,067 mm).

Regardless of the numerical dimensions of training pant 47, a percentage relationship exists between the overall product length L and flap front attached length LF and flap back attached length LB. If the overall product length is L, then flap front attached length LF is desirably between about 1 percent to about 40 percent of product length L, and flap back attached length LB is desirably between about 1% to about 45% of product length L. Similarly, flap active length AL is desirably between about 25 percent to about 90% of product length L.

Flap separation distance SD is related to flap width WP such that flap separation distance SD is generally between about 30 percent to about 60 percent of flap width WP.

Continuing to refer to FIGS. 6–7, flap elastics 67, which may be a single ribbon of elastic material or a plurality of strands of elastic material, should have a certain elasticity, elongation, and tension in order to assist in proper positioning of containment flaps 64 at the crotch of the wearer. In order for containment flaps 64 to assume the desired upright orientation, as illustrated in FIG. 7, to contact and seal against inner surfaces 52 of legs 50 (FIG. 5), each flap elastic 67 should have a minimum of about 90 percent elongation when incorporated into flap 64 of a finished training pant 47. A desired range of elongation is between about 90 percent to about 150 percent stretch. For example, if active flap length AL, which is the length of a flap elastic 67 that is elastically active, is 10 inches, then at 150 percent elongation, that flap elastic 67 would extend to a distance of 25 inches. A desired tension range for each flap elastic 67 is between about 90 grams to about 200 grams at 90 percent ultimate elongation.

Active flap length AL, flap separation distance SD, flap height HP, flap width WP, and the elastic characteristics of flap elastics 67 determine the anatomical location of corners 76 of well 86 at the crotch of the wearer. If active flap length AL is too long, or if the elastic characteristics of flap elastics 67 are not within the desired ranges, there is inconsistency in proper or correct flap positioning at the crotch of the wearer. Attached lengths LF and LB, along with flap separation distance SD, keep flaps 64 from shifting too close together into the crease of the buttocks during body movement. If containment flaps 64 shift too close together, they may form a tent over absorbent composite 70 and prevent any absorption of urine or other liquid waste matter. Furthermore, if flap separation distance SD is too great, flaps 64 will drag along the inner surfaces 52 of the wearer's legs 50, thereby resulting in the turned or folded-over condition as illustrated in FIG. 4. The present invention provides, among other features, consistent containment flap positioning within the crotch of the wearer as illustrated in FIG. 5, in which distal ends 65 of flaps 64 are at or near the crease of the body formed by the inner surfaces 52 of legs 50 with the crotch. Additionally, because of the relatively large dimension of flap height HP, as absorbent composite 70 becomes heavier due to the absorption of waste matter, containment flaps 64 will extend to continue to maintain a good seal as absorbent composite 70 begins to separate away from the crotch, as illustrated in FIG. 5.

Another unique feature of the present invention is a containment flap softness quality measured as the average actual drape value. The materials of which containment flaps 64 are made desirably have an average actual drape value less than about 1.83. This softness reduces red marking, irritation, and other effects at the sensitive crotch area. The test procedure for determining the average actual drape value is ASTM Standard D-1388 entitled "Stiffness of Fabrics" and Method 5206 Federal Test Methods Standard #191A. Equipment used was a Cantilever Bending Tester, Model 79-10 available from Testing Machines Inc., 400 Bayview Avenue, Amityville, N.Y. 11701; a 30"×30" precision paper cutter with sample holder; and a cutting press with ½"×6" rectangular cutting die. In performing this test, 5 products made in accordance with the present invention were selected and, prior to performing the test, each of the containment flaps were identified as the "left" and "right" containment flap with the product in the partially disassembled, stretched-out state, as illustrated in FIG. 6. The containment flaps were then removed from the 5 products to give a total of 10 containment flaps, which were cut into strips having a length of 6 inches and a width of ½ inch. These strips did not include flap elastics 67. Each strip was moved at a rate of 4¾ inches per minute in a direction parallel to its long dimension, so that its leading edge projected from the edge of a horizontal surface. The length of the overhang was measured when the tip of the strip depressed under its own weight to a point where the line joining the tip to the edge of the platform made an angle of 41.5 degrees with the horizontal. Once a strip depressed to the angle of 41.5 degrees, its length was measured, and the actual drape value was calculated by dividing the measured length in inches by 2. After performing this test on each of the 10 flaps from the 5 products, the 10 actual drape values were averaged to determine the average actual drape value.

In use, the wearer will position his or her feet through waist opening 60 and leg openings 62 and then grasp pant 47 and pull upwardly along legs 50. As pant 47 moves upwardly, there is an increase in the sliding contact pressure or friction between containment flaps 64 and inner surfaces 52 of legs 50. However, because of the above-described features of the present invention, containment flaps 64 will maintain their upright orientation, while pant 47 is pulled snugly into the wearers crotch. Containment flaps 64 will then be properly positioned, as illustrated in FIG. 5, in order to form well 86. As absorbent composite 70 becomes heavier due to its absorbing waste, absorbent composite 70 will tend to sag or move downwardly, away from the crotch. However, containment flaps 64 will be able to extend in height, as illustrated in FIG. 5, to maintain the seal against the crotch.

Figure 8:
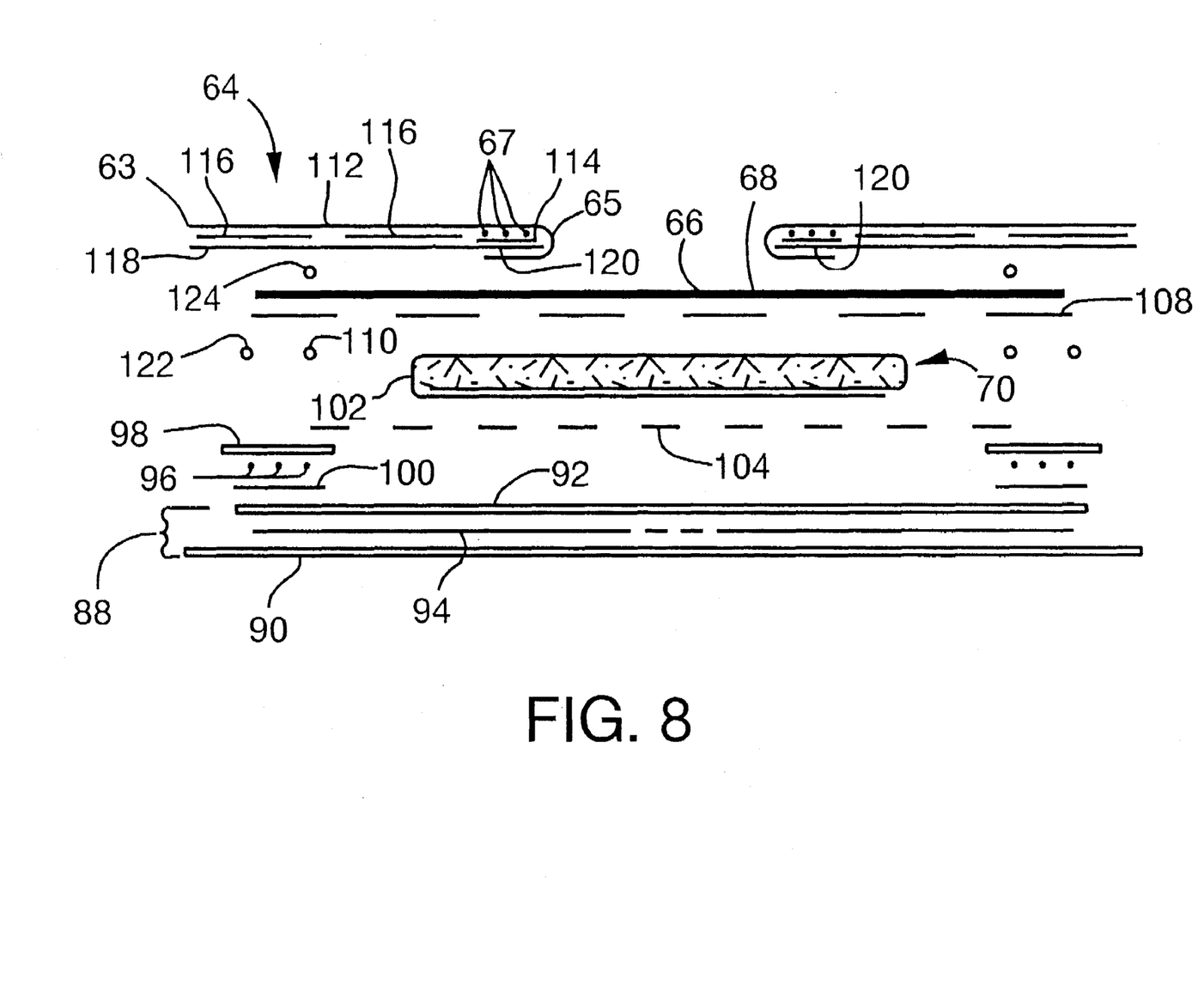
FIG. 8 is an exploded, fragmentary view of FIG. 7 with the containment flaps in a flat state.
Figure 9:
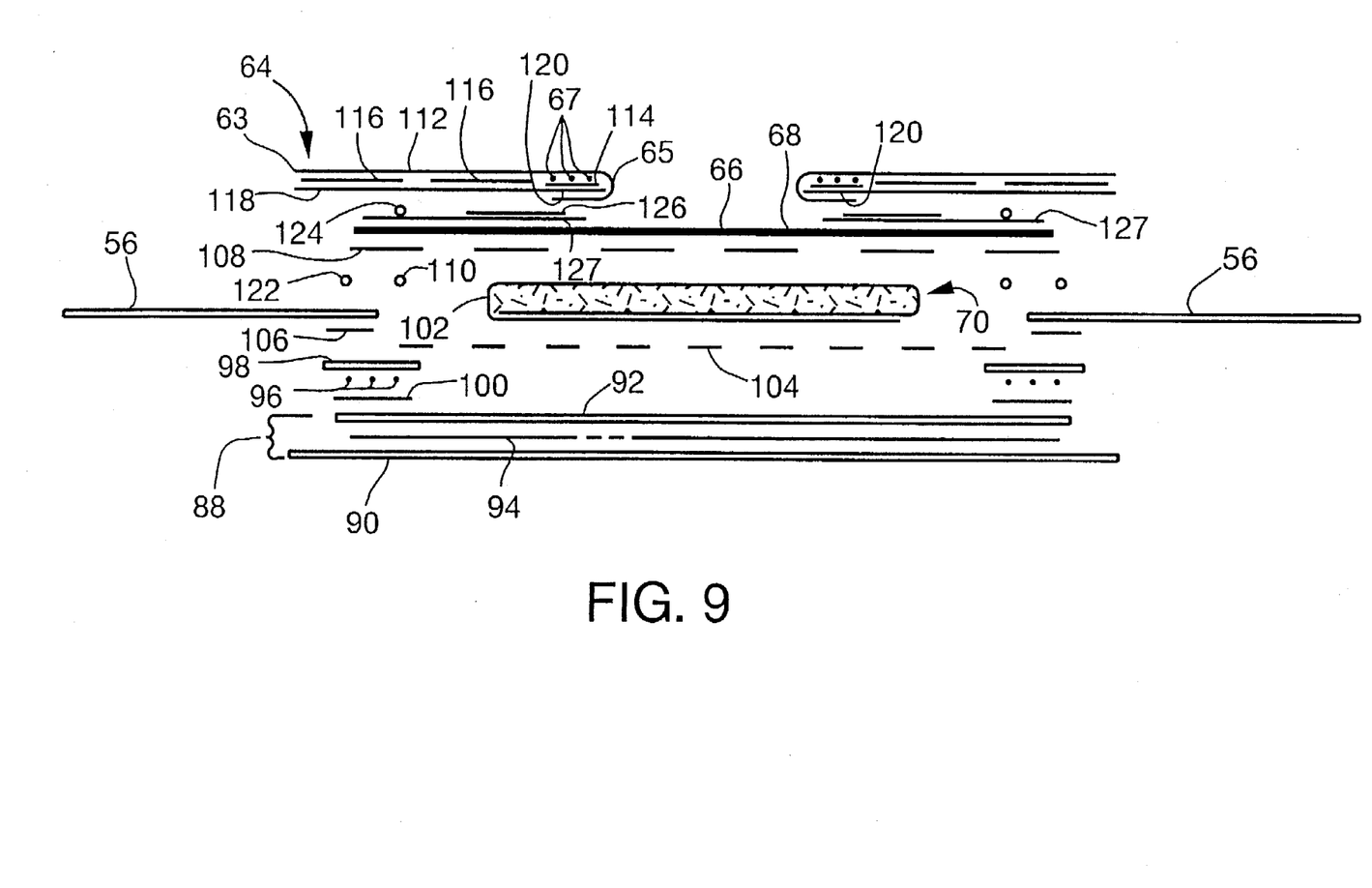
FIG. 9 is an exploded, fragmentary end view.

FIGS. 8 and 9 illustrate outer cover 88, which desirably is a two-layer composite including liquid permeable nonwoven layer 90 and liquid impermeable film layer 92 suitably joined together by adhesive 94. Outer cover 88 can also be a single layer comprising film layer 92, nonwoven layer 90, or any other suitable liquid permeable or liquid impermeable material. Carrier sheet 98 has 3 strands of leg elastic 96 adhesively attached thereto, while in a stretched condition, in any suitable manner known in the art. Carrier sheet 98, with leg elastics 96 attached thereto in a stretched condition, is adhesively attached to film layer 92 by leg adhesive 100. Absorbent composite 70 comprises a mixture of cellulosic pulp fluff and superabsorbent materials that are wrapped in tissue wrap 102 to provide integrity to the fluff/superabsorbent material mixture. Absorbent composite 70 can comprise only cellulosic pulp fluff, only superabsorbent materials, or a combination of both with other absorbent or non-absorbent materials. Absorbent composite 70 is adhesively attached in any suitable manner to film layer 92 by absorbent construction adhesive 104. Side panels 56 are suitably attached by side panel adhesive 106 to carrier sheet 98. Liner 66 is adhesively attached to absorbent composite 70 and film layer 92 by liner adhesive 108, and by adhesive bead 110 to carrier sheet 98. Referring specifically to a single containment flap 64, flap elastics 67, which are 3 strands of elastic material, are adhesively attached, while in an extended condition, to nonwoven layer 112 by elastic adhesive 114. Flap adhesive 116 is applied in any suitable manner to nonwoven layer 112, and film layer 118 is attached to nonwoven layer 12 by flap adhesive 116. Nonwoven layer 112, at its end near flap elastics 67, is folded over flap elastics 67 and film layer 118 and attached to film layer 118 by flap fold adhesive 120. Flap 64 is then attached by adhesively joining film layer 118 to side panel 56 by means of flap bead 122, which extends the full length of containment flap 64, and by means of flap seam adhesive 124, which also runs the full length of containment flap 64. Flap dead zones 80, 82 (FIG. 6) are formed by flap end adhesive 126.

Thereafter, side panels 56 are joined, such as by ultrasonic bonding, to form seams 58 (FIG. 5).

The materials of which training pant 47 are made, including containment flaps 64, can be any materials specifically desired by the user or manufacturer. Numerous examples of materials used in constructing training pant 47 are described in the aforementioned U.S. patents and applications incorporated by reference herein.

In one embodiment, side panels 56 are a stretch bonded laminate comprising an inner layer of a prestretched elastic meltblown core sandwiched between and attached to a pair of spunbond polypropylene nonwoven webs having a basis weight of about 0.4 oz/yd$^2$ (13.6 gsm). Suitable elastic materials can be purchased from the Shell Chemical Company of Houston, Tex. under the trade name KRATON.

Suitable adhesives can be obtained from Findley Adhesives, Inc. of Wauwatosa, Wis.

Flap elastics 67 in containment flaps 64 are strands of LYCRA T151 940 decitex elastic which can be obtained from E. I. DuPont De Nemours Co., Wilmington, Del. Nonwoven layer 112 is a spunbond polypropylene nonwoven web having a basis weight of about 0.7 oz/yd$^2$ (23.7 gsm), and film layer 118 is a 0.6 mil polyethylene film which can be obtained from Filmtech Corp. of Easton, Pa. It is desired that nonwoven layer 112 be liquid permeable, and that film layer 118 be liquid impermeable. Film layer 118 may also be vapor permeable, liquid impermeable, and film layer 118 may have portions thereof that are liquid impermeable with the other remaining portions being liquid permeable.

Bodyside liner 66 is liquid permeable and is a spunbonded polypropylene nonwoven web having a basis weight of about 0.75 oz/yd$^2$ (25.4 gsm ). Outer cover nonwoven layer 90 is a spunbonded polypropylene nonwoven web having a basis weight of about 0.8 oz/yd$^2$ (27.2 gsm), and outer cover film layer 92 is a 1.0 mil polyethylene film obtainable from Edison Plastics Co. of South Plainfield, N.J.

Carrier sheet 98 is a 0.75 mil polypropylene film which is liquid impermeable and can be obtained from Edison Plastics Co. of South Plainfield, N.J., and leg elastics 96 are 3 strands of LYCRA T151 940 decitex elastic which can be obtained from E. I. Du Pont De Nemours, Wilmington, Del.

Figure 10:
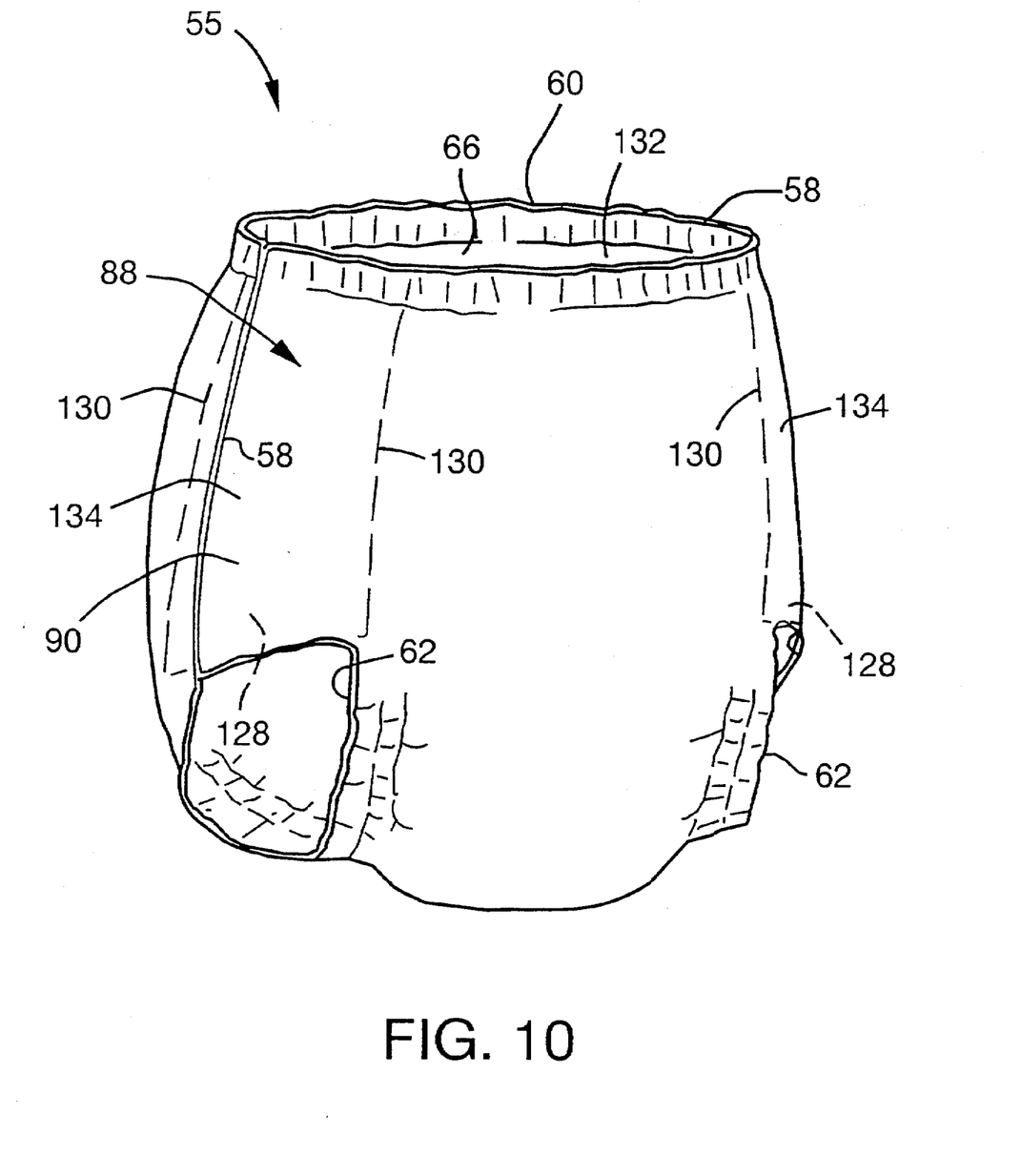
FIG. 10 is a perspective view of another embodiment of the present invention.

FIG. 10 illustrates another training pant 55 incorporating the principles of the present invention. A detailed description of the structure and function of training pant 55 is contained in the aforementioned U.S. patent application Ser. No. 809,993. Training pant 55 differs from training pant 47 in that outer cover 88 and liner 66 of waste containment assembly 61 extend to seam 58 to form waist opening 60 and leg opening 62, and elastic side members 128 are operatively joined to inner surface 132 of pant 55. Each elastic side member 128 terminates at elastic side member edges 130. Inner surface 132 at sides 134 can be liner 66, or, if liner 66 does not extend to seam 58, can be outer cover film layer 92. Further, if outer cover film layer 92 does not extend to seam 58, then inner surface 132 at sides 134 can be outer cover nonwoven layer 90. In any event, elastic side members 128 are joined to inner surface 32 at sides 134, and sides 134 can be suitably treated so as to stretch with side members 128. One method of treating sides 134 is mechanical treatment, such as aperturing to provide holes or slits that allow sides 134 to extend or stretch. Also, sides 134 can be made of an elastomeric material the same as or different from the material of which side members 128 are made.

While this invention has been described as having a preferred embodiment, it will be understood that it is capable of further modifications. This application is thereby intended to cover any variations, equivalents, uses, or adaptations of the invention following the general principles thereof, and including such departures from the present disclosure as come within known or customary practice in the art to which this invention pertains and fall within the limits of the appended claims.

What is claimed is:

1. A disposable absorbent article, comprising:
   a waste containment assembly having a length dimension,
   elastic side panels joined to said waste containment assembly to form a waist opening and a pair of leg openings,
   a pair of containment flaps operatively joined at their respective end portions in a transversely foreshortened state to said waste containment assembly,
   each said containment flap having a flap front attached length that is between about 1 percent to about 40 percent of said length dimension, and a flap back attached length that is between about 1 percent to about 45 percent of said length dimension, and
   a flap elastic in a distal end of each said containment flap, and having a tension range between about 90 grams to about 200 grams at about 90 percent ultimate elongation.

2. The article of claim 1 wherein said containment flaps have a flap separation distance less than about 3 inches.

3. The article of claim 2 wherein each said containment flap has a flap active length that is between about 25 percent to about 90 percent of said length dimension.

4. The article of claim 3 wherein said containment flaps have a flap separation distance and a flap width, said flap separation distance being between about 30 percent to about 60 percent of said flap width.

5. The article of claim 4 wherein each said containment flap has a distal end and a proximal end, said distal and said proximal ends being spaced apart a distance between about 1 inch to about 3 inches.

* * * * *